United States Patent
Fonash et al.

(10) Patent No.: US 10,390,724 B2
(45) Date of Patent: Aug. 27, 2019

(54) THREE-DIMENSIONAL BIO-MEDICAL PROBE SENSING AND CONTACTING STRUCTURES WITH ADDRESSIBILITY AND TUNABILITY

(71) Applicant: The Penn State Research Foundation, University Park, PA (US)

(72) Inventors: Stephen J. Fonash, State College, PA (US); Wook Jun Nam, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 576 days.

(21) Appl. No.: 14/901,243

(22) PCT Filed: Jun. 26, 2014

(86) PCT No.: PCT/US2014/044333
§ 371 (c)(1),
(2) Date: Dec. 28, 2015

(87) PCT Pub. No.: WO2014/210306
PCT Pub. Date: Dec. 31, 2014

(65) Prior Publication Data
US 2016/0374585 A1    Dec. 29, 2016

Related U.S. Application Data

(60) Provisional application No. 61/876,582, filed on Sep. 11, 2013, provisional application No. 61/861,852, (Continued)

(51) Int. Cl.
*A61B 5/00* (2006.01)
*A61B 5/053* (2006.01)

(52) U.S. Cl.
CPC ............ *A61B 5/053* (2013.01); *A61B 5/685* (2013.01); *A61B 2562/028* (2013.01); (Continued)

(58) Field of Classification Search
CPC ............ A61B 5/685; A61B 2562/0209; A61B 2562/028; A61B 2562/0285; A61B 2562/04
See application file for complete search history.

(56) References Cited

U.S. PATENT DOCUMENTS 4,837,049 A * 6/1989 Byers ............... A61B 5/0422
216/11
6,188,783 B1   2/2001 Balaban et al.
(Continued)

FOREIGN PATENT DOCUMENTS

JP   2004085392 A   3/2004
WO      0030534 A1   6/2000
(Continued)

OTHER PUBLICATIONS

James J. Jun, Nicholas A, et al., Fully integrated silicon probes for high-density recording of neural activity. Nature 551, 7679 (2017).
(Continued)

*Primary Examiner* — Sean P Dougherty
(74) *Attorney, Agent, or Firm* — Dinsmore & Shohl LLP

(57) ABSTRACT

A three dimensional biomedical probe device is provided that includes a planar substrate. A probe structure is supported on the planar substrate. The probe structure has a base and a portion essentially perpendicular to the base extending along a length to a tip and has a linear dimension at the tip of said probe structure of between 5 nanometers (nm) and 5 microns thereby defining an AC, DC, or transient current, charge, or voltage sensing probe. In one variation, this probe is the electrical contact to the biomedical medium. In
(Continued)

another variation, this probe is also the gate electrode of a field effect transistor (FET). An array of selectively electrically addressable such devices is also provided giving the ability to sample the physiological activity at many positions within cells, fluids and intercellular regions without the need for mechanical motion and inducing cellular lysis.

25 Claims, 12 Drawing Sheets

Related U.S. Application Data filed on Aug. 2, 2013, provisional application No. 61/839,523, filed on Jun. 26, 2013.

(52) U.S. Cl.
CPC .............. *A61B 2562/0209* (2013.01); *A61B 2562/0285* (2013.01); *A61B 2562/04* (2013.01)

(56) References Cited

U.S. PATENT DOCUMENTS

| | | | |
|---|---|---|---|
| 6,515,346 B1 | 2/2003 | Kemeny | |
| 6,936,194 B2 | 8/2005 | Watts | |
| 7,603,153 B2 | 10/2009 | Jacobsen et al. | |
| 8,367,035 B2* | 2/2013 | Rogers | B82Y 10/00 423/447.3 |
| 8,666,471 B2* | 3/2014 | Rogers | A61B 5/05 600/377 |
| 9,196,765 B2 | 11/2015 | Yang et al. | |
| 2004/0065252 A1 | 4/2004 | Sreenivasan et al. | |
| 2004/0065976 A1 | 4/2004 | Sreenivasan et al. | |
| 2006/0054941 A1 | 3/2006 | Lu et al. | |
| 2006/0070868 A1* | 4/2006 | Fan | B82Y 40/00 204/173 |
| 2008/0009763 A1* | 1/2008 | Chiou | A61B 5/0408 600/373 |
| 2008/0063585 A1* | 3/2008 | Smalley | B82Y 10/00 423/414 |
| 2009/0220561 A1* | 9/2009 | Jin | A61K 9/0009 424/423 |
| 2009/0283425 A1* | 11/2009 | Clark | A61B 5/04001 205/792 |
| 2010/0213963 A1* | 8/2010 | Yoshikawa | G01R 31/2896 324/756.03 |
| 2010/0279179 A1 | 11/2010 | Farrow et al. | |
| 2011/0304317 A1 | 12/2011 | Shalev et al. | |
| 2012/0037591 A1 | 2/2012 | Tringe et al. | |
| 2012/0041337 A1* | 2/2012 | Ferguson | A61M 37/0015 600/573 |
| 2012/0283119 A1 | 11/2012 | Miyahara et al. | |
| 2012/0319705 A1* | 12/2012 | Schober | A61B 5/685 324/658 |
| 2013/0134546 A1* | 5/2013 | Cheng | A61B 5/04001 257/506 |
| 2013/0164522 A1 | 6/2013 | Pei et al. | |
| 2013/0165861 A1* | 6/2013 | Ross | A61B 17/205 604/173 |
| 2013/0225956 A1* | 8/2013 | Huang | A61B 5/0537 600/345 |
| 2013/0253299 A1* | 9/2013 | Weber | A61B 5/4519 600/377 |
| 2017/0156652 A1* | 6/2017 | Qiang | A61B 5/14865 |

FOREIGN PATENT DOCUMENTS

| | | |
|---|---|---|
| WO | 2012064177 A1 | 5/2012 |
| WO | 2014210306 A1 | 12/2014 |

OTHER PUBLICATIONS

The Economist; Neuroscience; Probing for Answers; A new nerve-cell monitor will help those studying brains; Nov. 11, 2017.

International Search Report and Written Opinion for co-pending international application No. PCT/US2014/044333, dated Oct. 28, 2014.

Nabar, B.P. et al., "A nanoporous silicon nitride membrane using a two-step lift-off pattern transfer with thermal nanoimprint lithography," J. Micromech. Microeng. 22 (2012) 045012 (8 pp).

* cited by examiner

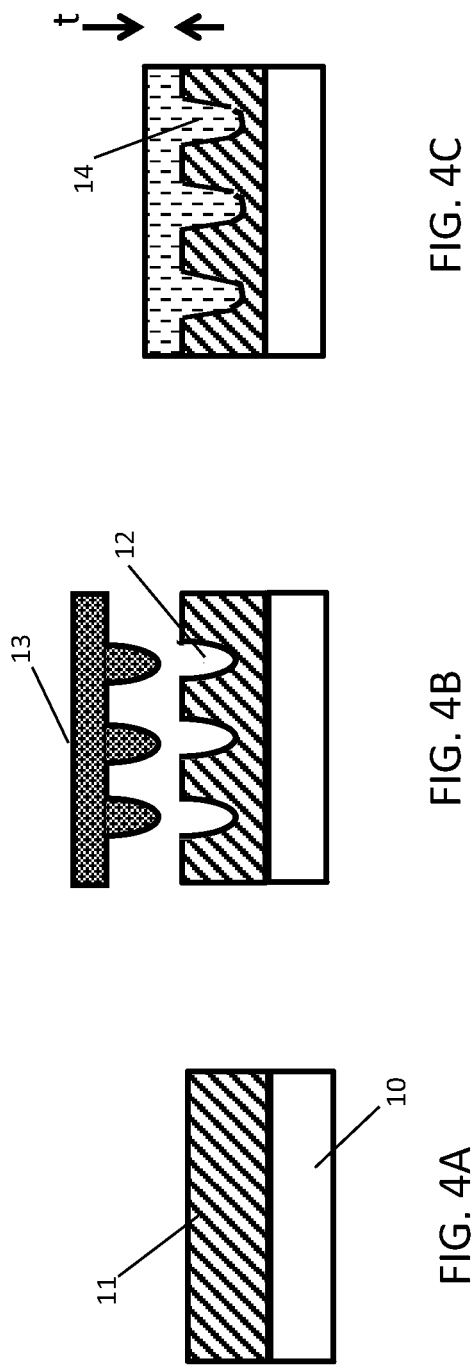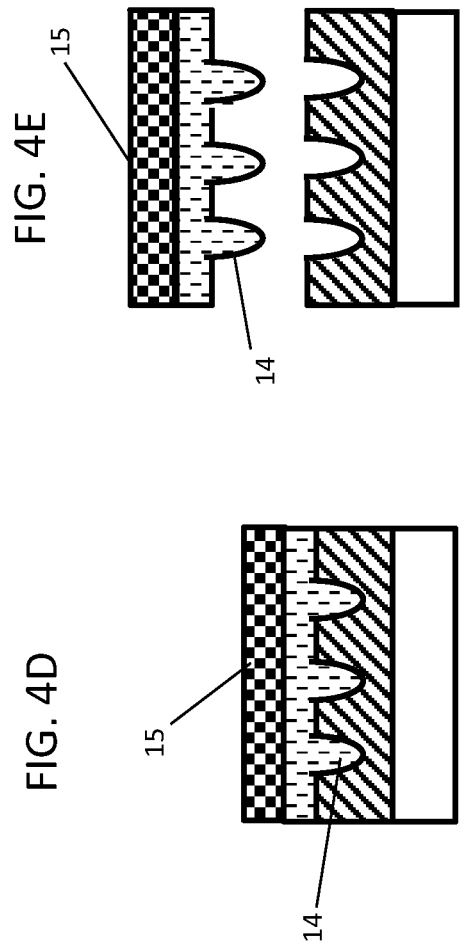

THREE-DIMENSIONAL BIO-MEDICAL PROBE SENSING AND CONTACTING STRUCTURES WITH ADDRESSIBILITY AND TUNABILITY

REFERENCE TO RELATED APPLICATIONS

This application claims priority to U.S. Provisional Application Ser. No. 61/839,523, filed Jun. 26, 2013; 61/861,852, filed Aug. 2, 2013; and 61/876,582, filed Sep. 11, 2013, the contents of which are incorporated herein by reference in their entirety.

STATEMENT OF GOVERNMENT SUPPORT

This invention was made with government support under Grant No. DUE1205105, awarded by the National Science Foundation. The Government has certain rights in the invention.

FIELD OF THE INVENTION

The present invention in general relates to the field of biological and medical sensing and contacting structures including clinical applications; and in particular, it relates to the design, fabrication, and utilization of three dimensional probe sensing or contacting structures configured as single devices or as arrays.

BACKGROUND OF THE INVENTION

Intracellular sensing and body fluid sensing are in demand for a variety of applications from patient monitoring to cell sorting and basic cell function studies. Bio-medical sensors are being developed that can continuously track a wide variety of physiological metrics and activities. Examples include tracking heart rhythm, blood pressure, respiratory rate, the oxygen saturation of hemoglobin, blood glucose concentrations, brain-computer interfacing, and brain waves. Many of these sensors are being integrated with electronics to provide wireless communication. Existing approaches to the sensing needs include voltage-sensitive optical dyes (1, 2) and single-terminal glass (3-5) or carbon (6-8) microelectrodes.

However, these bio-medical sensors have all met with limited acceptance owing to various technical issues. In particular, voltage-sensitive dyes have limitations including pharmacological side effects and phototoxicity (7, 8). While microelectrode probes allow mechanical insertion into tissue and cells, the requirement of either or both direct ionic and electrical contacting between probe tips and cell materials imposes difficult size constraints on this type of probe due to current-drawing (impedance) problems. Both voltage sensitive dyes and microelectrode probes are not amenable to in situ signal amplification, or to formation of an addressable-array Spatially localized, three-dimensional (3-D), electrically addressable, probe field effect transistor (FET) bio-medical sensing devices would avoid these difficulties. FETs can detect by monitoring the gate (G) electrode current, but they also have the basic advantage that they can sense by detecting gate charge variations without the need for particle current exchange with media such as cellular medium or body fluids; thus, interfacial impedance effects can be minimized. In addition, because signals can be detected by charge changes at gate surfaces, FETs can detect cellular potential (2-5), as well as biological molecules (1). FETs can measure ion flux or electrical signals in cells including neurons. The FET gate electrodes can also be functionalized (e.g., coated by the purposeful chemical bonding of various molecules such as antibodies, antigens, or ligands) to probe for the presence of very specific bio-chemicals within a cell. Unfortunately, FETs require, in addition to a gate electrode, two current flowing electrical contacts, the source (S) and the drain (D). Because of this, almost all biomedical sensing field-effect transistor (FET) probe devices that have been explored have not been 3-D. FET probes have been created with the sensing gate regions, as well as the sources and drains, all on the same planar substrate (9, 10), making design of 3D FET probes and their minimally invasive insertion into a cell or tissue a substantial challenge to-date. An exception to this planar arrangement limitation is a 3-D FET sensing probe device demonstrated by Tian et al. (9); however, that device still had several limitations that included: (a) incorporating the whole FET including gate electrode, source and drain portions in the probe rather than simply the sensing gate region; (b) did not use gate functionalization for specificity; (c) is composed of a source-gate-drain silicon (a brittle material) probe inserted into the cell medium; (d) did not utilize a well-defined gate dielectric; (e) is fundamentally limited to sizes dictated by its Si probe interconnects; and (f) is not amenable to roll-to-roll manufacturing.

Human cells vary from nerve cells with characteristic sizes of about 10 microns to heart cells with characteristic sizes of about 50 microns. In studies of basic probe dimension requirements, it has been found that tip sizes of ~200 nm to 5 μm are a compromise between being small enough to rupture cell membranes and penetrate into a cell with minimum damage (must be <5 μm) and large enough to yield a contact impedance in current drawing applications that is sufficiently low (must be >200 nm) (1, 2, 11-14).

Thus, there exists a need for a three dimensional biomedical probe sensing structure that has one or more of the attributes of (a) including a self-contained reference-electrode capability if desired, (2) electronic addressability, and being (3) amenable to use with wireless communication circuitry.

SUMMARY OF THE INVENTION

A three dimensional biomedical probe device is provided that includes a planar substrate. A probe structure is supported on the planar substrate. The probe structure forms a well or has a base and a portion essentially perpendicular to the base extending along a length to a tip and has a linear dimension at the tip of said probe structure of between 5 nanometers (nm) and 5 microns thereby defining an AC, DC, or transient current, charge, or voltage sensing probe. In one variation, this probe structure is the electrical contact to the biomedical medium. In another variation this probe structure is the gate of a field effect transistor (FET), while also being the electrical contact to the biomedical medium. In this case less than a complete complement of transistor components of a gate electrode, drain, channel, source, or gate dielectric are in underlying physical and electrical communication with said probe structure.

An array of selectively electrically addressable such devices is also provided giving the ability to sample the physiological activity at many positions within cells, fluids and intercellular regions without the need for mechanical motion and inducing cellular lysis.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying figures in which, relative scale is distorted for visual clarity, where like numerals used with respect to multiple figures corresponds to similar materials and structures. These drawings include:

FIGS. 4A-4E are schematics of a working mold approach to fabricating a sensing probe or an array of sensing probes of this invention using imprinting. The working mold material starts unpatterned on a working substrate as seen in FIG. 4A. At least part of the imprinted pattern for the probe array of this example is shown imprinted into the working mold material in FIG. 4B. The probe material or materials are seen disposed into the cavities of the probe pattern in FIG. 4C giving a thickness t between cavity regions. Device and circuitry processing is done after FIG. 4C. A substrate is seen to be present in FIG. 4D and is utilized to accomplish separation from the working substrate as seen in FIG. 4E;

DESCRIPTION OF THE INVENTION

Figure 1:
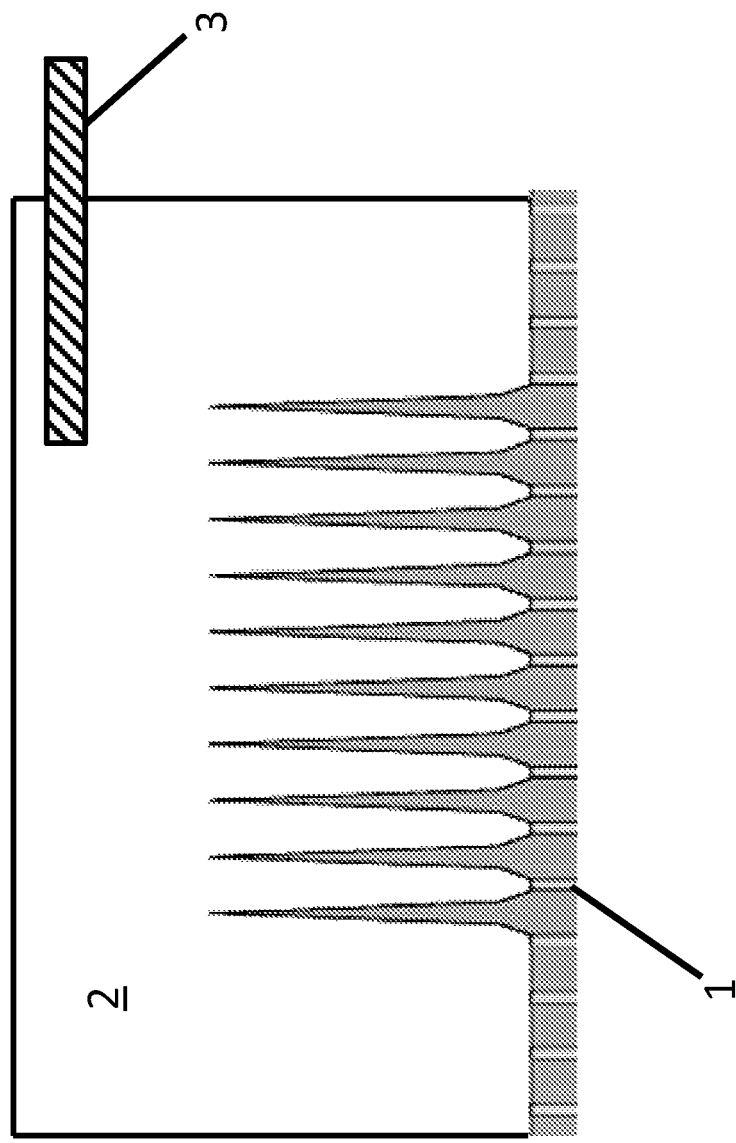
FIG. 1 is a schematic of exemplary prior art microelectrode probes.

The present invention has utility for design, process, and application of three dimensional (3-D) probes for biomedical sensing and contacting structures configured as single devices or as arrays. In some embodiments, the individual probe structures are addressable. An inventive probe structure may be used in a current sensing or contacting electrode configuration, or in a current or charge sensing field effect transistor configuration. These probe structures may also be used to deliver or detect impulses. Inventive probe structures in some embodiments include an integrated field effect transistor (FET) at each probe site. An inventive three dimensional probe structure architecture is configured in some embodiments for transduction or light emission as well as entity extraction from, or injection into cells, intracellular medium and body fluids.

Inventive 3-D micro- and nano-electrode probe and probe FET sensing devices are provided herein that address the limitations of the prior art. Due to their design, these devices can be arranged in fully electrically addressable arrays. In the case of the probe FET variation, the devices are (a) a truly 3-D sensor with the sensing gate electrode perpendicular to the plane of the source and drain, (b) employing a nano- to micro-scale gate electrode for biomedical (cell, intercellular, tissue and body fluid) medium insertion and monitoring, (c) being amenable to gate functionalization to enhance specificity, (d) having advantageous mechanical properties, (e) having advantageous interconnect architecture, and (f) being amenable to low cost roll-to-roll manufacturing. Such inventive micro- and nano-electrode and FET probes and arrays also have the advantage of being able to be moved into 3-D contact with a medium. These devices have the further advantage of being able to probe into and through a functioning cell without cell lysis due to their shapes and dimensions.

In addition one may operate these devices in mechanically movable, electrically addressable or both modes of attaining multiple measuring sites. The electrically addressable array configuration micro- and nano-electrode and FET probe approaches have the unique advantage of being able to be moved into contact with, and thereby probe systematically and electronically into, several regions of a cell, of cells, and of body fluids without subsequent mechanical motion. When multiple site probing is accomplished by selective reading of multiple probe/sensor positions using an addressable electronic array, multiple positions can be read (addressed) without the need for physically moving the array. If multiple probing is accomplished physically, this can be done using a stepper. A stepper apparatus is readily provided to move an inventive array a controlled distance between sampling positions. Of course when multiple site measurements are taken electronically by addressing probes of an array, the spacing is automatically controlled by array spacing. Such 3-D biomedical sensing micro- and nano-electrode and FET probe single or array configuration probe structures must have probes that are minimally invasive and therefore small enough to penetrate tissue or a cell while retaining cellular metabolic function. According to the present invention, nanometer- and micron-scale electrodes as well as FET types, overcome all the current issues hindering bio-medical probe development and utilization with respect to biomedical medium monitoring with probe dimensions within required basic probe dimensions for cellular penetration.

In some inventive embodiments, such micro- and nano-electrode and FET probe single probe structures are perpendicular to a planar substrate. In the FET probe variation the substrate contains the corresponding source and drain regions for FETs and in still other embodiments may contain devices and circuitry for addressability so as to retain a cellular scale dimensionality to the probe while affording complex functionality and ancillary features. Since it is perpendicular to the planar substrate, such as the previously mentioned controlled probe selection and reading, an inventive probe or probe array is freely positioned and inserted within a cell, intracellular region, or body fluid region for monitoring and data collection.

It is appreciated that a three dimension probe structure according to certain embodiments of the present invention are configured for transduction and are formed of a piezoelectric material and used to deliver or detect mechanical excitations. Similarly, the 3-D probe structure of the present inventions can be used to detect or cause light emission. In this case the probe may contain a junction; e.g., metal-semiconductor, p-n, or p-i-n configurations. In still other inventive embodiments, an inventive probe structure is modified to have a micro- or nano-pore at its tip to enable species (e.g., ions, molecules) extraction from, or injection into, cellular or intracellular media or body fluids. It is appreciated that the complementary form of tip is a well. A well-shaped probe structure is well suited for monitoring extra-cellular fluids and with an array of such probe structures, to perform such monitoring with spatial resolution. It is further appreciated that an array of both well-shaped probe structures and tipped probe structures is readily formed.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4. With respect to perpendicularity as detailed herein, essential perpendicularity includes angles within 20 degrees of othronormality.

Exemplary prior art probes of a penetrating microelectrode array configuration are seen in FIG. 1. These typically have sharp shanks, with base widths of ~80 micro-meters, lengths of approximately 1.5 mm and pitches of ~400 micrometers (15). As seen the prior art probes are on a substrate 1 and have penetrated some medium 2 (e.g., an intracellular region).

Figure 2:
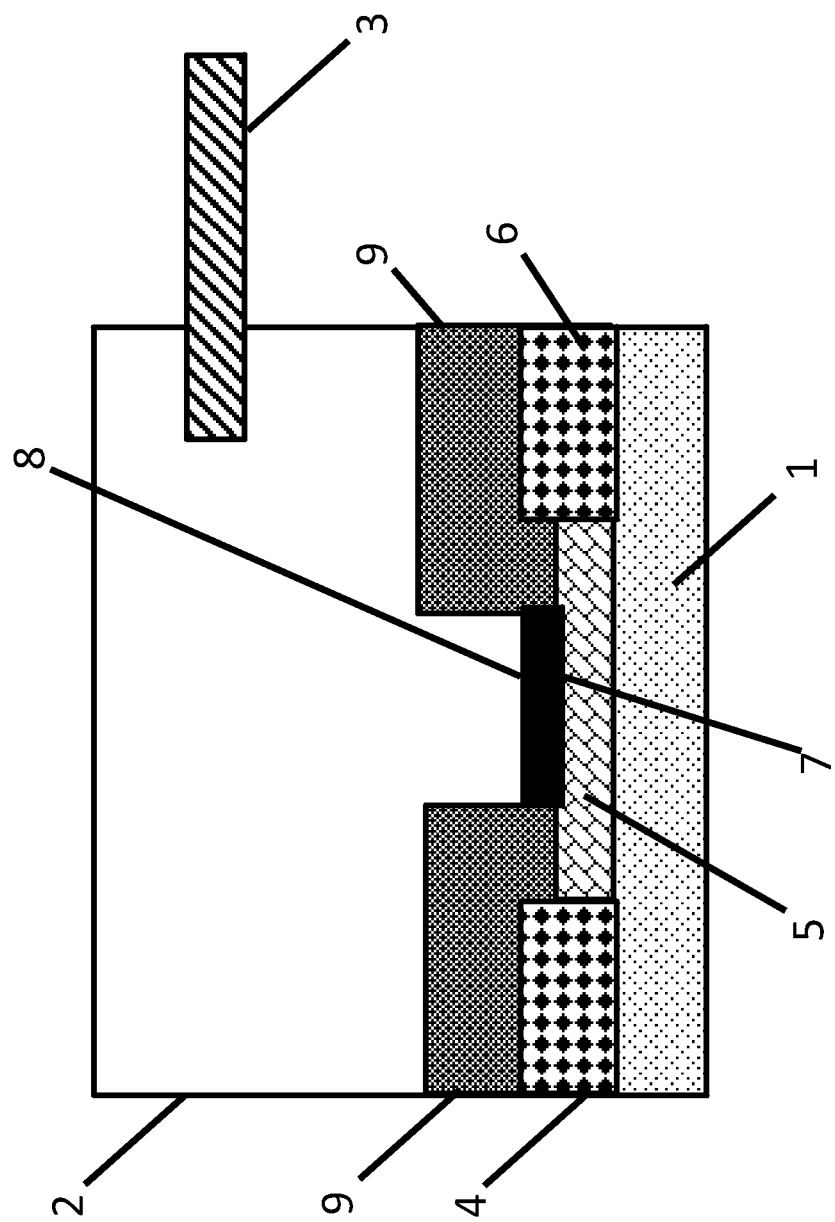
FIG. 2 is a depiction of an exemplary prior art FET sensor structure.

A reference electrode 3 may be present, as shown. An exemplary prior art FET sensor structure is seen in FIG. 2. It is typified by having a source 4, transistor channeling-bearing region 5 with its gate electrode region 7, and a drain 6 all positioned on a planar substrate 1, as indicated. In prior art applications, the gate electrode region 7 often does not have the advantageous gate dielectric 8 on 7 shown in FIG. 2. Volume 2 is the medium being probed and 3 is a reference electrode. Material 9 is an electrical insulator for isolating the transistor, except at the sensing gate electrode region 7, from the medium to be tested 2. This transistor structure may be a conventional transistor, a thin film transistor (TFT), or a nano-wire or ribbon transistor. It may be an inversion or accumulation device.

Figure 3:
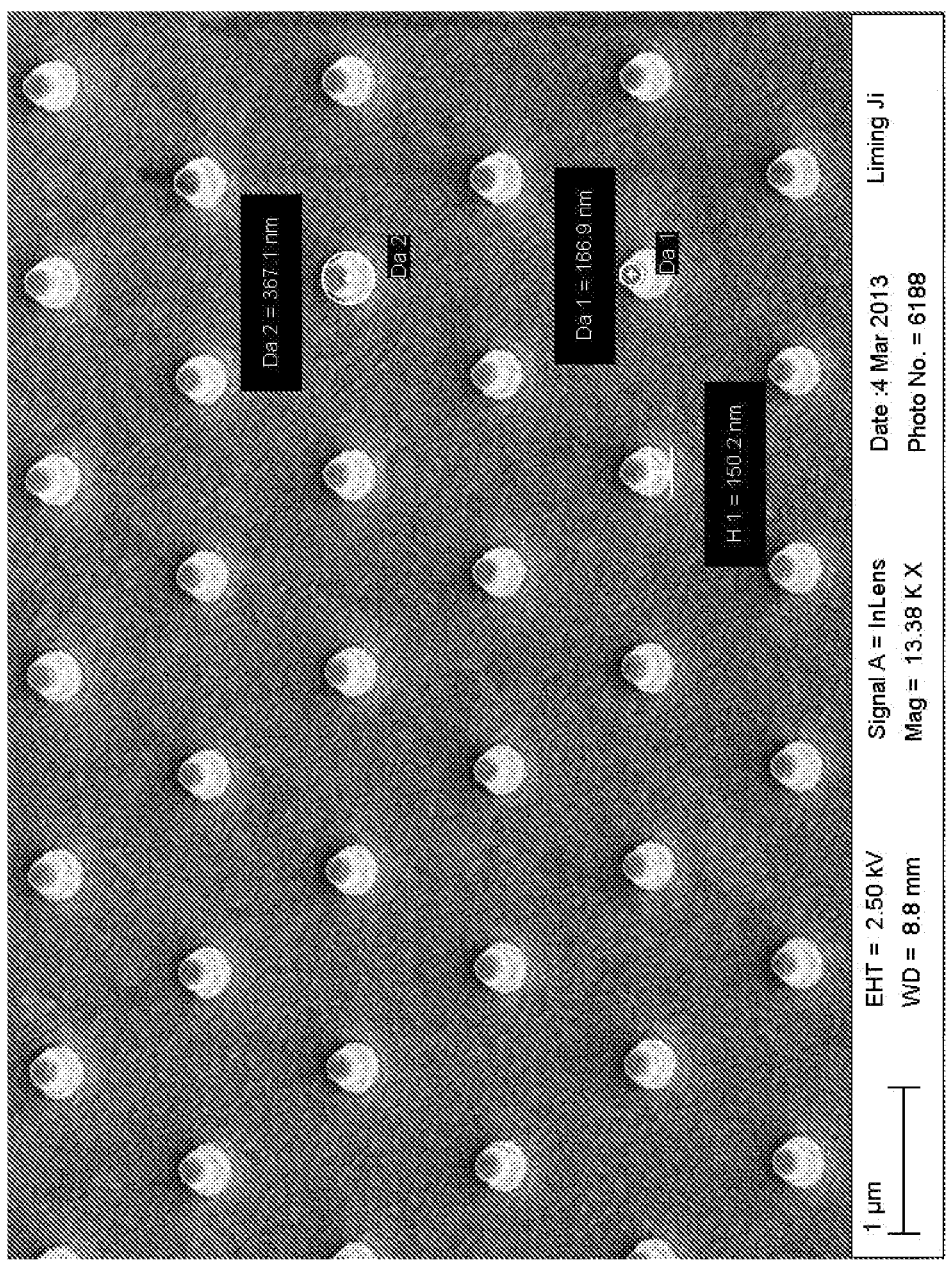
FIG. 3 is a field emission scanning electron microscopy (FESEM) micrograph showing a top view of an actual array of probes from an example of the innovative 3-D biomedical probe sensing structures of this invention. This view of the nano-element array of cone-like probes is at a 30 degree angle.

FIGS. 1 and 2 are contrasted with FIG. 3 in which an inventive probe structures are shown in a FESEM micrograph in an actual, exemplary array of the 3-D probe structures possible with this invention. As may be noted, the characteristic dimensions of these particular exemplary probes of this invention are in the nano-scale range or slightly above. In general such dimensions may be in the micro- or nano-scale as needed to comply with the application and the ideal probe size constraints discussed earlier; i.e., tip sizes can be approximately 5 nm to 1.0 micron or more in diameter as needed for rupturing cell membranes and for having a tolerable impedance when used for current drawing applications. Probe lengths are typically from 100 nm or less to microns.

The probes seen in FIG. 3 are in an array but they can be in a single probe configuration also. If in an array, the probe spacing and probe dimensions (e.g., largest diameter and height) can vary with position. Inventive probes are readily formed of a variety of materials. These materials are readily disposed sequentially by some combination of growth, physical positioning, electrochemical deposition, self-assembly, physical vapor or chemical vapor deposition (including close spaced sublimation) techniques. In the example of FIG. 3, the probes are Ag which has been deposited by sputtering. The outstanding flexibility in terms of the material from which an inventive probe structure is formed, dimensionality, and arrangement on a substrate found in this invention is due to the probe design and a novel fabrication sequencing which allows a process flow exploiting nano-imprinting/nano-molding methods. Using these methods with working molds gives the designs of this invention outstanding sensing and contacting capabilities, the possibility of using flexible substrates, full electronic addressability (reading) capability and compatibility with using highly manufacturable roll-to-roll processing flow, as seen in FIGS. 4 and 5.

Figure 5D:
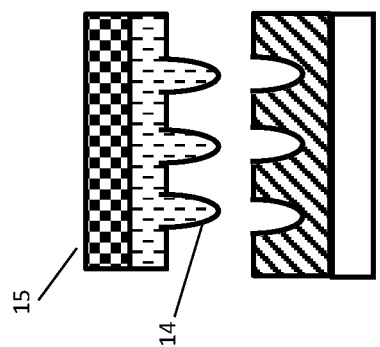
FIGS. 5A-5D are schematics of a working mold approach to fabricating a sensing probe or an array of sensing probes of this invention using molding. The working mold material is patterned by molding and positioned on a working substrate as seen in FIG. 5A. These figures show at least a part of the pattern of a probe array in the working mold material. The probe material or materials are seen disposed into the cavities of the probe pattern in FIG. 5B giving a thickness t between cavity regions. Device and circuitry processing is done after FIG. 5B. A substrate is seen to be present in FIG. 5C and is utilized to accomplish separation from the working substrate as seen in FIG. 5D.
Figure 5C:
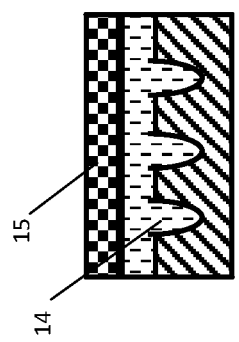
Figure 5B:
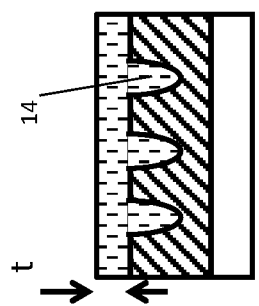
Figure 5A:
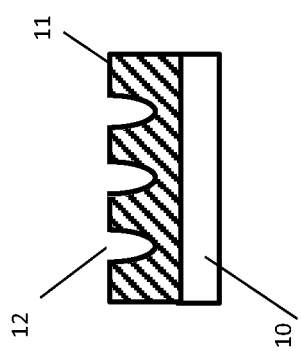
Figure 6:
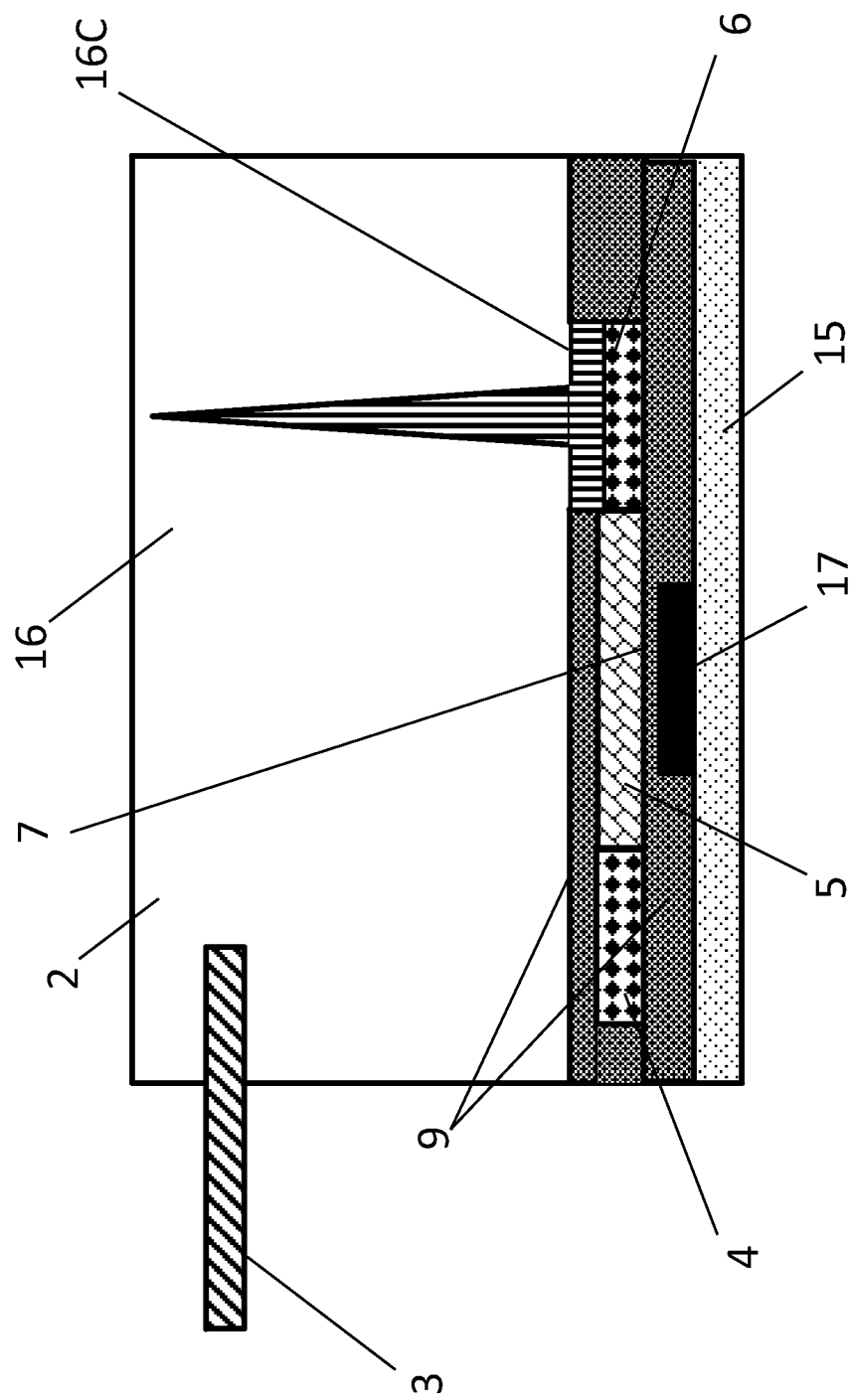
FIG. 6 is a cross-sectional schematic of an exemplary nano- or micro-electrode 3-D voltage sensor/current-drawing sensor including an inventive probe structure.
Figure 8:
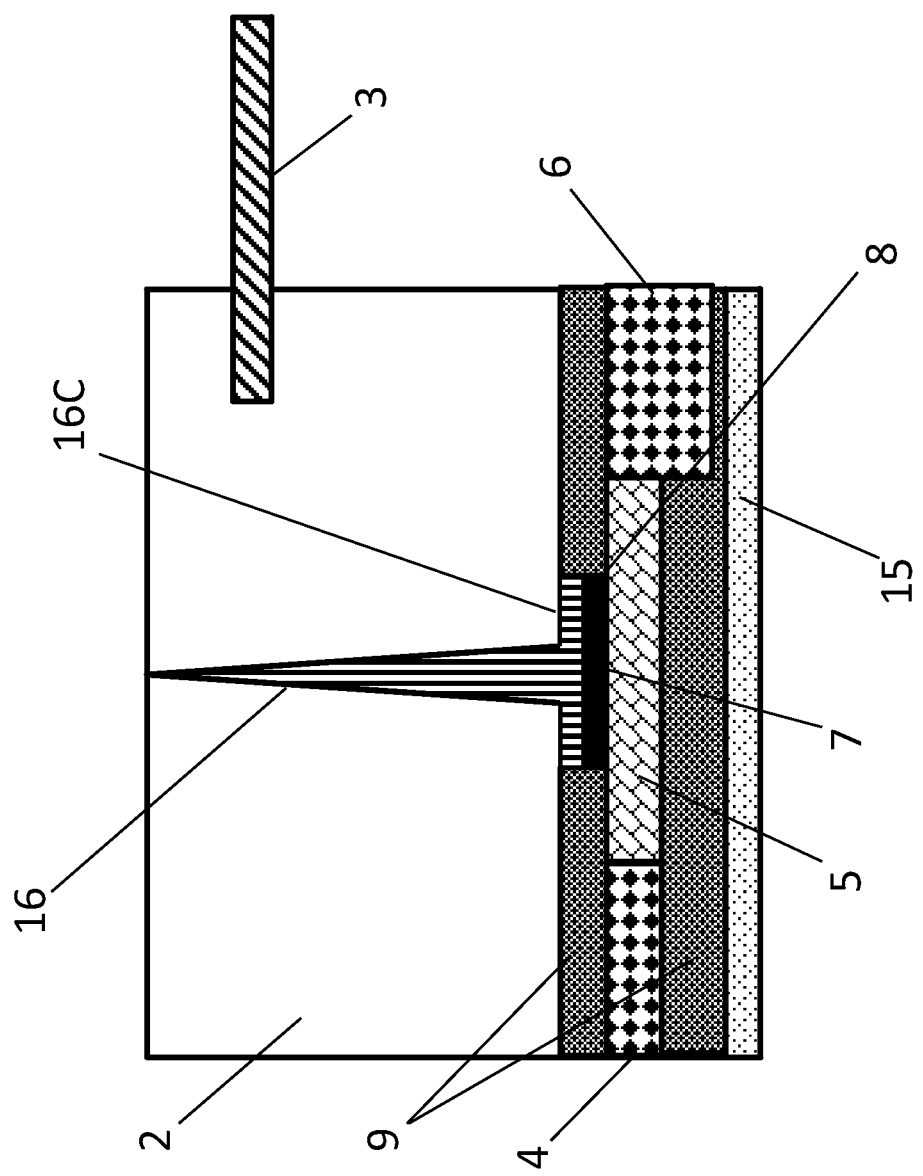
FIG. 8 is a cross-sectional schematic of an exemplary nano- or micro probe 3-D FET sensor including an inventive probe structure, where the probe 16 and its base 16C are the conductor (or semiconductor) of a FET gate electrode structure. This may be a stand-alone probe or part of a probe array.
Figure 9:
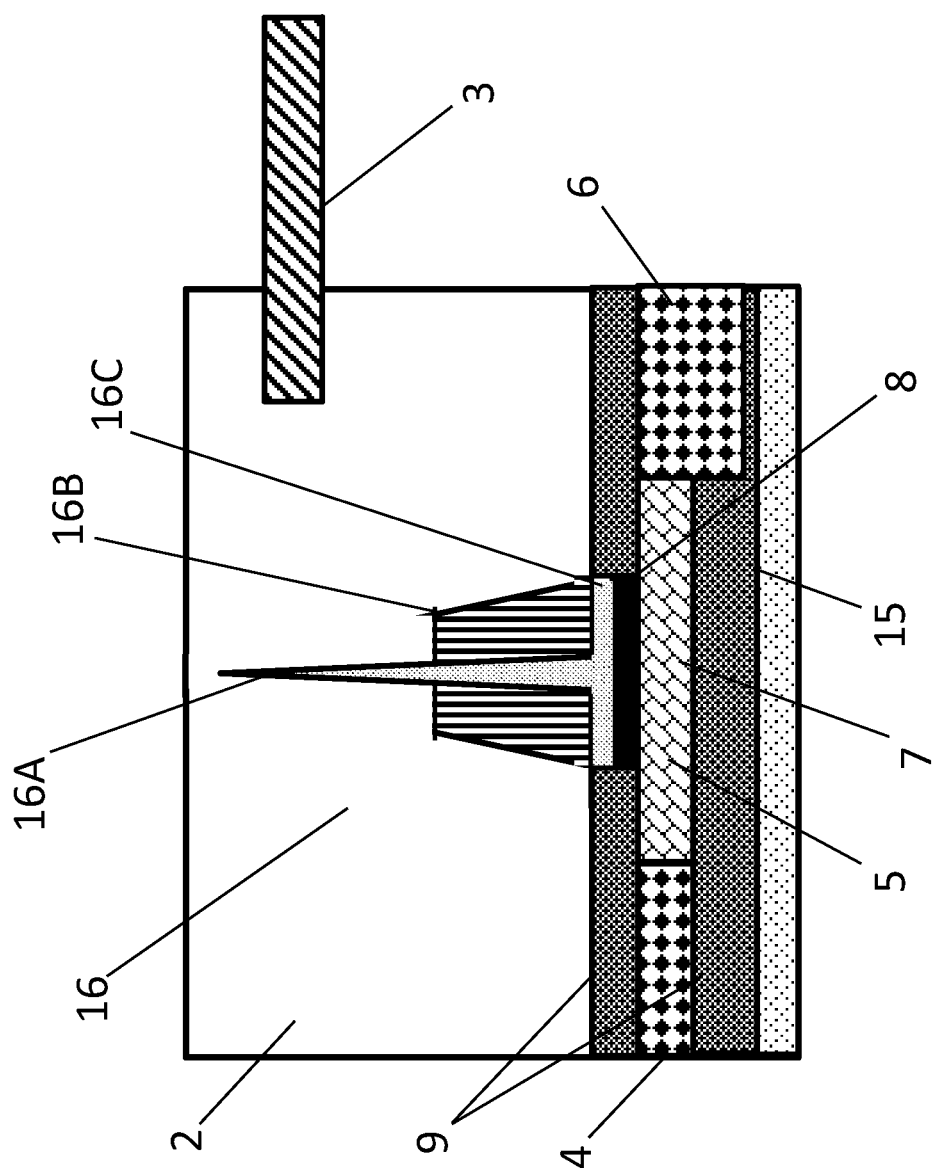
FIG. 9 is a cross-sectional schematic of another exemplary nano- or micro-probe 3-D FET sensor of this invention. This may be a stand-alone probe or part of a probe array. The probe and its base are on the gate dielectric and together with this dielectric constitute the gate structure in this example. The probe portion of the gate electrode is perpendicular to the source, channel, and drain and is seen penetrating the cell medium. The probe of this example is seen to be composed of two different materials which is accomplished by sequential disposition into the cavity. This unique probe material variation capability allows for limiting probe-medium electrical communication to the region at the probe tip. A separate reference electrode may be used (shown) or built-in (not shown) using an adjacent region, probe or probes.

The nano-imprinting/nano-molding methods of fabrication employed in this invention use a working mold material 11 seen with a cavity pattern 12 in FIG. 4B (nano-imprinting approach) and FIG. 5A (nano-molding approach). In either approach, a working substrate 10 may be provided. In the imprinting approach, the original working mold material of FIG. 4A is imprinted to form cavities 12 as seen in FIG. 4B. In the nano-molding approach, a liquid (or vapor) precursor to the solid working mold material is disposed in a master mold and solidified yielding the patterned working mold of FIG. 5A. As seen in FIG. 4C or 5B, a subsequent step in either approach is to position the probe material or materials 14 into the empty cavities and inter-cavity regions of FIG. 4B or FIG. 5A. The thickness t in FIG. 4C or 5B may be of the same material as the probe material or may be a different material and is adjustable, as needed. After the base (16C of FIG. 6) is disposed and lithographically defined, devices, circuit elements and interconnects to these and the probe back contacts as well as interconnects, and transistor structures for, or incorporating the probes, may be fabricated. Standard lithography (e.g., photolithography, stamping), etching, and other processing, as needed, may be used for establishing the required patterns. An example showing a nano- or micro-electrode 3-D voltage detecting/current-drawing sensor of this invention is seen in FIG. 6. The base 16C, processed from the inter-cavity and cavity regions, and the probe 16, produced by the cavity filling are seen. The depiction in FIG. 6 shows the nano- or micro-electrode 3-D probe in series with a FET (e.g., a TFT); however, it should be appreciated that such a FET need not be present if addressability in, for example, an array is not required. In one variant the probe is incorporated into a transistor allowing for FET detection and in-situ amplification. Examples resulting in probe incorporation into transistors are seen in FIGS. 8 and 9. The final substrate 15, disposed after the required processing, is seen in FIGS. 6, 8, and 9. The separation from the working substrate 10, seen in FIGS. 4E and 5D, is undertaken after substrate 15 is present. An alternative to fabricating the required devices and circuit elements in situ is to prepare them elsewhere, stamp such elements on, and then dispose the final substrate 15. The working mold material of 10 is removed by conventional chemical phenomena (e.g., etching or dissolution), physical phenomena (e.g., mechanical separation), or both. This removal in some inventive embodiments involves external energy sources such as heat, ultra violet (UV) radiation, or the like. It is appreciated that the inventive probe structures are readily formed as a stand-alone probe or one element of a probe array. In the case of FET sensors, the probe and its base are on the gate dielectric of the sensing FET and together with this dielectric constitute the gate electrode structure. The probe is essentially perpendicular to the source, channel, and drain and is seen penetrating a biomedical medium (e.g., a cell, an intercellular region, or body fluid region) in FIGS. 6, 8, and 9. A separate reference electrode may be used (shown) or built-in (not shown) using an adjacent region, probe or probes.

The working mold material 11, with empty cavities 12 into which material or materials are disposed to form probes such as those seen in the array example of FIG. 3, is prepared by creating a master template. If this master template is used to produce imprinting templates, the master template is formed using standard techniques such as lithography and etching to have what is termed the positive of the desired array pattern. The master template is then used to produce the imprinting template which then is a negative. The imprint template is forced, using conventional imprint techniques, into contact with a mold material creating the working mold material with the positive array pattern, which is the desired pattern into which material or materials are disposed creating the device. Alternatively, if this master template is used to produce patterned mold material directly without imprinting, it has what is termed the negative of the desired array pattern. The master template is then used to produce the working mold material, which is positive, by positioning a liquid or vapor precursor of the working mold material into the master template. This step is followed by a curing of this precursor employing various chemical, physical, or both treatments including heating and radiation exposure (e.g., ultra violet (UV)). The resulting array of cavities in the mold material is the pattern into and onto which material or materials are disposed in creating the device in this molding approach.

It is noted that in either the imprinting or molding approach, the master template can be used multiple times to create multiple positive mold material arrays. In the case of molding, this merely requires reuse of the master template. In the case of imprinting, the forming of the needed positive mold templates can be done directly or by forming sequences of positive/negative pattern formation templates. Mold material 11 of FIGS. 3 and 4 include organic and inorganic materials. These materials illustratively include polymers (e.g., polyimide), spin-on-glass types, sol-gels (e.g., SnO, $TiO_2$ sol-gels), and other such materials. Mold materials 11 are removable by physical or chemical techniques (e.g., etching) to allow exposure and use of the probe structures formed in the molds.

Figure 10:
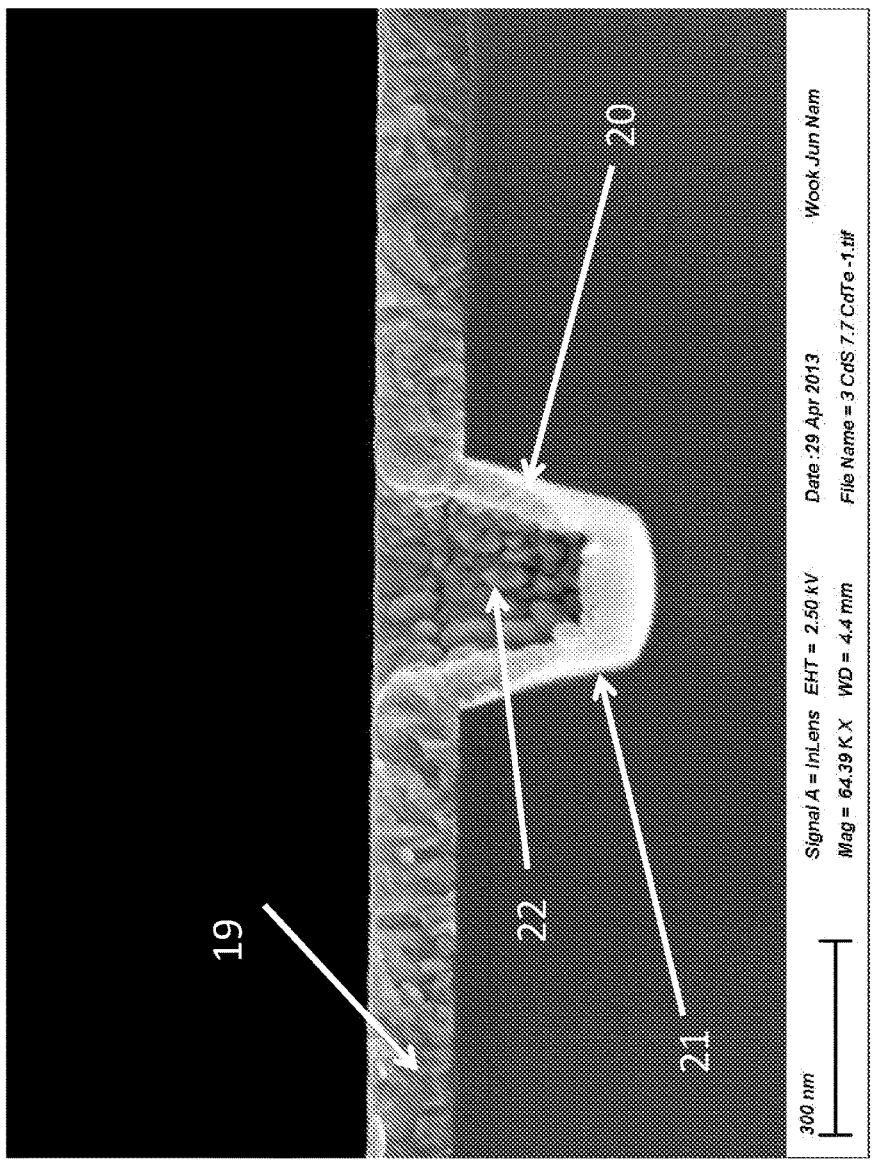
FIG. 10 is a cross-sectional FESEM showing the results of a deposition of material onto a working mold. The film produced by the deposition parameters used in this example is seen in the inter-cavity region and in a cavity in a working mold. The parameters have been chosen here so as to not fill the cavity.
Figure 11:
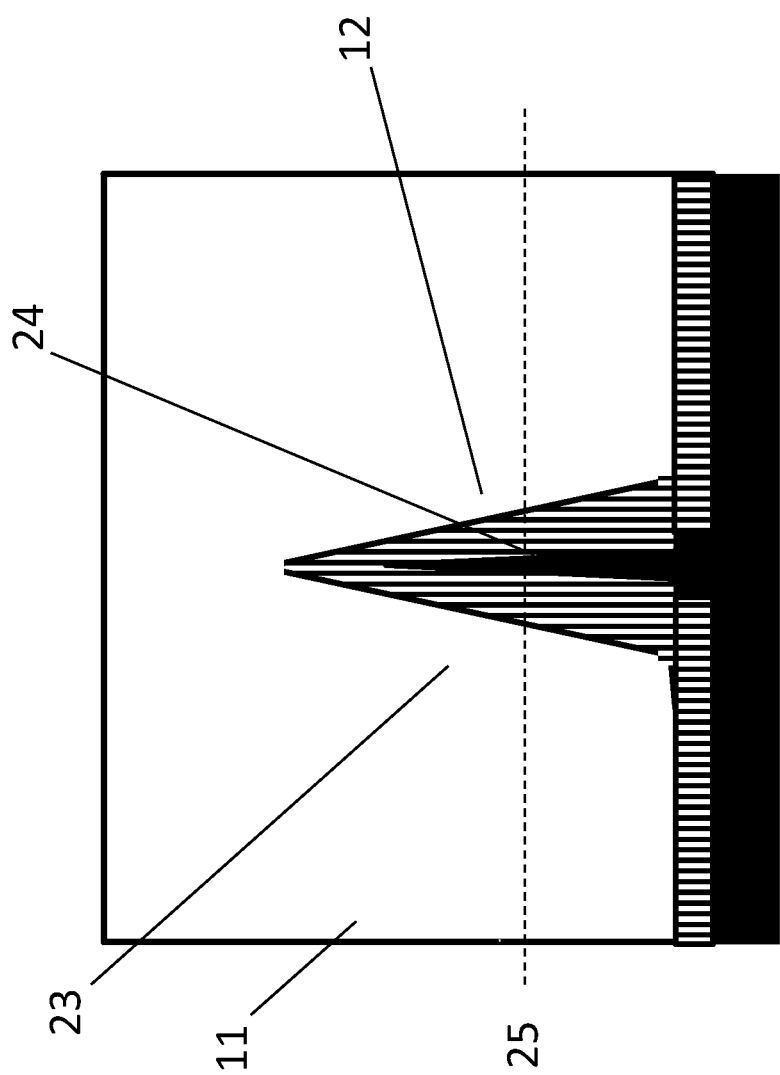
FIG. 11 is a cross-sectional schematic showing a cavity in the mold material into which materials have been sequentially disposed.

The disposing of probe material into the cavities and inter-cavity regions of a working mold material for forming probes for sensing and contacting structures includes disposing probe material or materials, or probe material precursors, into the cavities and inter-cavity regions as required for the desired use. These probe materials that are intended to collectively including multiple probe materials and probe material precursors illustratively include semiconductors, insulators, metals, and piezoelectrics. These probe materials in some inventive embodiments are in the form of particles when disposed. It is further appreciated that in some inventive embodiments that a combination of organic and inorganic substances are employed. Semiconductors, using sequential disposition of semiconducting materials and/or dopants into the cavities 12, are utilized in some inventive embodiments to form probes with various functions including diode behavior for radiation and temperature sensing, as well as light emitting or light sensing structures. Metal and semiconductor probe structures are used as a conductor or semiconductor, respectively, for transistor gates (e.g., as in FIGS. 8 and 9) or as simply contacts (nano- and microelectrodes) to the medium (FIG. 6). In either case the actual electrically active region of a probe may be positioned (See FIG. 9) deep in the medium 2, using a probe composed of two (or more) materials. This may be accomplished by sequentially disposed materials positioned in the cavity. Having these at least two materials may be exploited to have a probe with an electrically active upper region 16A and electrically insulating lower region 16B as depicted in FIG. 9. Achieving the electrically active probe tip-only situation of FIG. 9 is accomplished, for example, by disposing a first material into the cavities as seen in the FESEM of FIG. 10. As seen in FIG. 10, processing parameters and cavity aspect ratio and shape have been chosen to have material 23 (see FIG. 11) disposed on the cavity bottom 21, side walls 20, and the inter-cavity region 19 in such a manner that a void 22 is produced. A second (conducting) material 24 is then disposed into the void resulting in the structure schematically represented in FIG. 11. The probe type of FIG. 9 then results by etching or otherwise removing the mold 11 and material 23, which is an insulator or can be converted into an insulator, down to example level 25 shown. Material 23 in other embodiments is an insulator or a metal that can be readily anodized into an insulator skin for 16B and 16C of FIG. 9. In other embodiments, material 23 can be a material such as gold (Au) onto which an insulator can be formed by self-assembly. With remaining mold material removal, probe 16 is in a configuration with 16B and 16C being covered with an insulator film. It is noted that the void due to the parameters of the disposition of material 23 (See FIG. 10) and the cavity parameters or a remaining void after disposing material 24, allowed by the parameter selection, can also be useful. If line 25 intercepts such voids, the result after etching down to 25 is a hollow probe. Such probes, especially since they are amenable to operating as sensors, or the probes can be biased and used for transporting substances such as ions or small molecules into or out of a cell medium or body fluid region.

Figure 7:
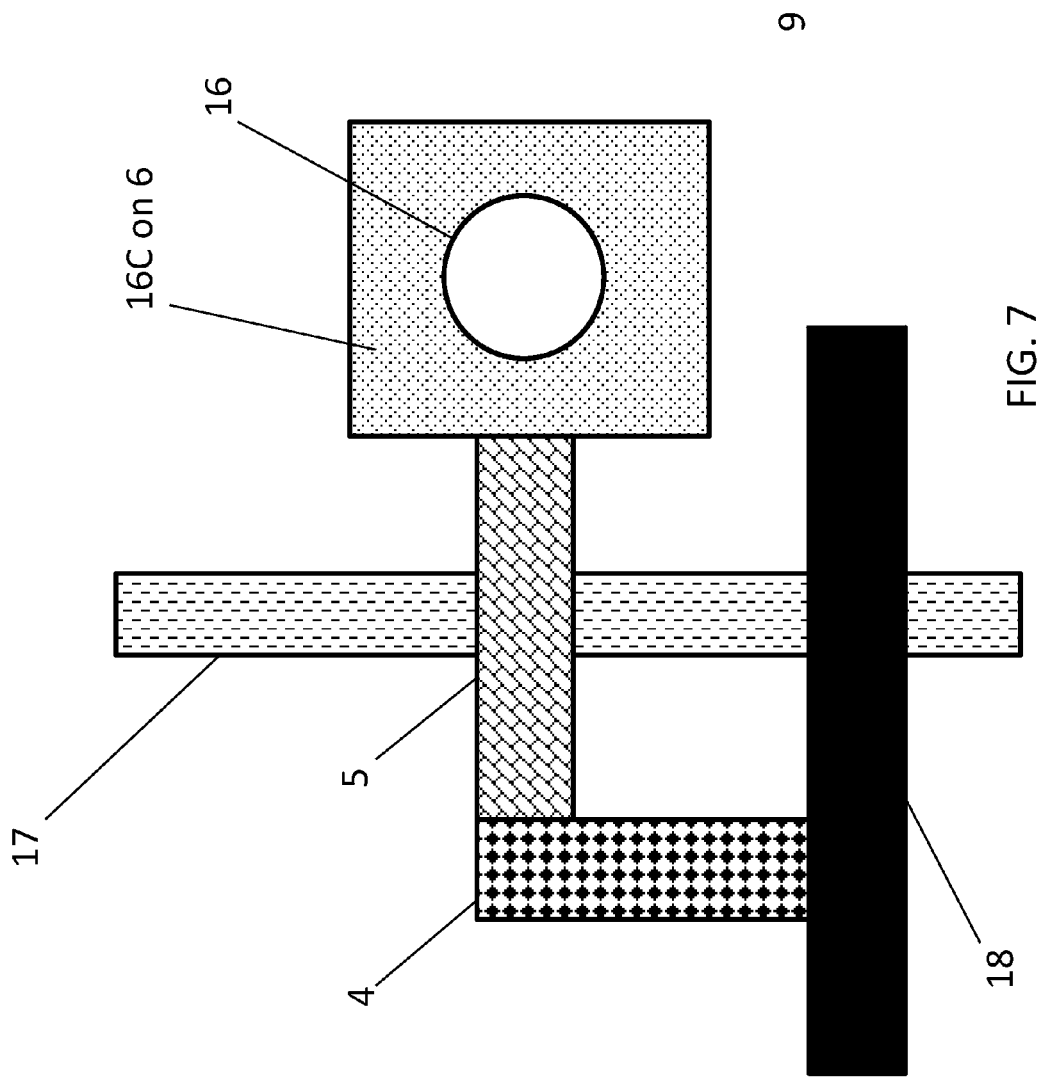
FIG. 7 is a top-view schematic showing a possible interconnect layout for the nano- or micro-electrode sensor of FIG. 6. This may be a stand-alone probe or part of a probe array. In this variation, the sensor probe uses a FET for addressability only. The insulator 9 of FIG. 6 is everywhere in this example between the FET, driver line, and data interconnect elements.

The insulator 9 of FIGS. 6-8 may serve as the gate dielectric of the transistor structure. Piezoelectric materials are used in some embodiments for the probe structure in cases where mechanical disturbances need to be created or sensed. It is appreciated that an inventive probe structure may be functionalized with, for example, molecules (e.g., antibodies, antigens, proteins, etc.) or nanoparticles or a combination thereof; using well known techniques to give them one or more of specificity, increased sensitivity, and catalytic activity.

The mold cavities 12 are in some embodiments are wider at the molding opening as compared to the mold bottom for facilitating disposing of materials into cavities and also for facilitating subsequent separation. The working mold material is chosen to be compatible with the processing and processing temperatures to which the working mold material will be exposed. The disposing of probe structure materials into cavities and inter-cavity regions of the mold template is accomplished by using one or more of a variety of physical and chemical deposition techniques such as physical or chemical vapor deposition, in situ growth, and atomic layer deposition, as well as by employing stamping and impressing techniques (e g, impressing nanoparticle slurries into the cavities). The one or more materials are disposed into the cavities and inter-cavity region, by whatever means that is effective. There may be one cavity, multiple cavities, and cavity arrays and the latter may be arranged in a repetitive lattice pattern (e.g., hexagonal, triangular, square), as desired.

The probe structures resulting from this design and processing comprise a 3-D bio-medical probe residing on a planar substrate 15. The composition of the latter may include "flexible" materials such as polymers or metal foils. These probe structures may be used singularly, in multiple arrangements, and in arrays. The 3-D nature of these probe sensor/contacting structures and the possible interconnect architectures for connectivity, electronic addressability, and amenability to low cost roll-to-roll manufacturing are distinct advantages over prior art bio-medical sensing/contacting devices. The incorporation of these probes with or into FET structures gives active, addressable sensing devices which are 3-D, can function as current, voltage, or charge sensors, only utilize probe (as opposed to full FET) insertion, are amenable to chemical or nano-particle functionalization for enhanced specificity, can have advantageous mechanical properties due the wide choice of probe materials, have an advantageous interconnects architecture, and are unique innovative bio-medical sensors. Further, the processing flow used in their fabrication may be implemented as a batch or continuous flow. The latter flexibility affords the ability to perform the processing in a roll-to-roll manner.

The present invention is further detailed with respect the following non-limiting examples. These examples are intended to provide details regarding specific embodiments of the present invention and not to limit the appended claims to the scope of these examples.

EXAMPLES

In these examples, transistor structures, when used, are depicted as typical MOSFET (FET) inversion-type devices each with a source and drain region. However, to simplify doping the FET semiconductor, an accumulation mode MOSFET (AMOSFET) type transistor may also be used (16) removing the need for specifically doped source and drain regions. In either case the transistors may be TFTs, nano-ribbon devices, nano-wire or tube devices.

Example 1

In this example, single or multiple metal electrical probes are formed as seen in FIG. 4C or 5B and as dictated by working mold design and/or subsequent dicing or cutting. When an array of such probes is formed, the result is seen in FIG. 3, an example which has a hexagonal lattice arrangement that is constant with position. However, lattice type (e.g., square, hexagonal), probe shape (e.g., column-like, cone-like, hemisphere-like, dome-like), probe spacing L, probe height h, and maximum width d (giving aspect ratio h/d) can all be adjusted in the original mold design and can vary with position.

In the design of this example, two different materials can be sequentially disposed into an empty cavity to form the probe 16. A first material is disposed to ultimately form the lower portion of the probe 16B of FIG. 9. This material is chosen for its being an insulator such as SiO2 or for its ability to be processed to create an insulator on its surface. In either case the role of this material is to render 16B and 16C and the lower portion of the probe incapable of electrically communicating with the medium 2. Further, the material, cavity, and processing parameters are chosen in this example to produce a void as seen in FIG. 10. A second material such as Pt is disposed into this void. With the removal of the mold material and $SiO_2$ down to line 25 of FIG. 11 and subsequent removal of all the mold material, the exemplary Pt probe 16A of FIG. 9 is formed. While this example is a Pt probe, other metals and semiconductors may be utilized. While the FET sensor configuration of FIG. 9 has been used in this discussion, when this type of probe is completed, it may be used as a nano- or microelectrode or as a FET gate electrode probe as seen in FIG. 9. When in use, this probe penetrates the medium and very uniquely only communicates with the medium using the tip region of 16A depicted in a FET gate structure in FIG. 9.

In the case of nano- or micro-electrode probes, electrical connectivity requires at least an interconnect line to the sensing probe and connectivity to a reference electrode. This reference structure may be another adjacent probe or probes, an option which when exercised renders a separate reference electrode 3 (or electrodes) unnecessary. Such interconnects may be fabricated, after the unpatterned full base layer corresponding to base layer 16C is defined, by lithography (e.g., photolithography), etching, and other processing, as needed. For example, simple lithographic or stamping patterning of the full base layer to isolate the probes but leave interconnects is straightforward and may be used in establishing the required patterns. When such nano- or microelectrode probes are used in series with a FET (e.g., a TFT) as seen in FIG. 6, each nano- or micro-electrode in an array becomes electrically addressable. It is appreciated that the probe depicted is operative as a stand-alone probe or one element of a probe array. The probe and its base are on a drain (source) in this example and the probe is essentially perpendicular to the drain (source) bearing substrate and is seen penetrating a medium (e.g. cell, intercellular region, body fluid region or tissue). The probe is seen to be in series with a FET which may be addressed to allow or disallow data collection from that specific the sensor. The probe may be composed of two (or more) materials with lower region and base electrically isolated from the medium.

The interconnects are patterned with the data lines 18 and driver lines 17 of FIG. 7 obviously isolated electrically from one another as seen in this example.

In the case of multiple probes (e.g., an array) each probe may be made addressable and/or selected probes may be chosen to play the role of the reference electrode 3. Addressability and built-in reference electrode formation, if used, are accomplished by forming the devices and circuitry needed before disposing the substrate 15 and before separation from the working substrate 10. Addressable nano- and micro-electrode probes are achieved as seen in FIGS. 6 and 7. As seen in FIG. 6, each addressable transistor is driven by a FET (e.g., by a TFT) that accessed by a driver line 17 and a data line 18 depicted in FIG. 7. Current flow from (or to) the probe, from the source 4 through the drain 6 and therefore through data line of the probe-controlling transistor occurs when the driver line is biased to turn on the transistor. This arrangement across the array gives specifically positioned bio-medical data from the probe 16 inserted into the bio-medical medium. This information can be wirelessly transmitted and/or can be used to construct an image. The latter is possible with both the nano- and micro-electrode probes and TFT-type sensor probes due to the addressable array opportunities of this invention. Both can be accomplished with additional circuitry at the array periphery or added to the substrate 15. The required reference (counter) electrode needed may be one or more probes in the array which are configured to have a single interconnect and need not be addressable. These may be positioned systematically about each addressable probe further enhancing the positing of the data collection. Further, the probes of this example may have the probe functionalized to enhance specificity and sensitivity. Current-drawing probes of this example can be used to sense using variations in the probe current.

The required circuitry may be fabricated as discussed above or pre-formed circuitry may also be used and positioned, for example, by stamping. The required circuitry is formed or positioned before disposing the substrate 15 and before separation from the working substrate 10. All the probe finishing steps such as etching or etching and anodization (e.g., those of FIG. 11) are undertaken after separation from the working substrate 10.

Example 2

In this example, metal electrical probes are formed as depicted in FIG. 4C or 5B and used as the gate electrode of an FET (e.g., TFT) as seen in FIGS. 8 and 9. As may be noted, the base 16C of the probe resides on a gate dielectric 8. The gate dielectric 8 and the probe base 16C have the same pattern in this example. The result may be a single FET or an array of multiple FET sensors, as dictated by working mold design or subsequent dicing or cutting. When an array of probes is formed, the lattice arrangement, spacing L, probe shape (e.g., cone-like, column-like, dome-like), probe height h, and maximum width d are all adjustable and can vary with position across the array. When a single FET probe only is desired, connectivity requires two interconnect lines (for the source and drain) to the sensing FET probe and connectivity to the separate reference electrode 3. In either the single probe or multiple probe cases, the separate reference electrode 3 may be eliminated and a reference structure may be another adjacent probe, or probes, only used for this reference function and therefore only having one interconnect. This option renders a separate reference electrode (or electrodes) unnecessary. The distinguishing feature of this design is that the gate function is dictated by the 3-D probe which resides on the gate insulator 8 and penetrates into the medium being sensed.

Figure 12:
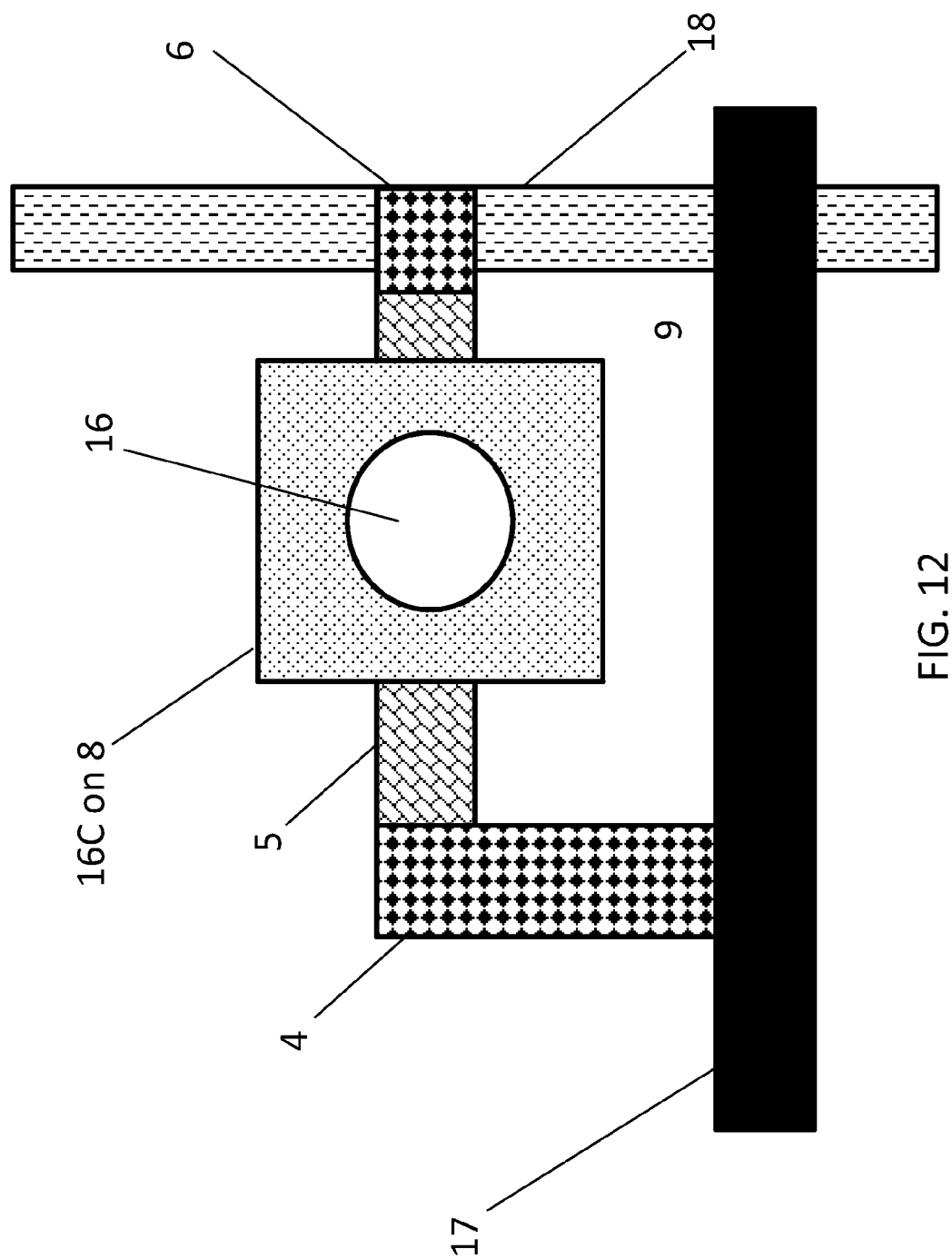
FIG. 12 is a top-view schematic showing one possible interconnect layout for the nano- or micro FET sensors of FIGS. 8 and 9. This may be a stand-alone probe or part of a probe array. In this example the insulator 9 is everywhere between the FET, driver line, and data interconnect elements.

As may be seen from FIG. 12, an interconnect arrangement can allow each probe FET to be individually addressed and read-out. While various addressing schemes may be used, in this simple example of FIG. 12, the sensor is being operated in the gate charge variation detection mode, gate electrode current is assumed negligible and all driver lines 17 except the one shown are at open circuit. The required FET elements, contacts, interconnects, and circuitry are fabricated after the base in FIG. 4C or 5B has been disposed. In an exemplary processing sequence, the base 16C is defined by standard processing (e.g., photolithography and dry etching) and the insulator 9, which may also be the material used as the gate insulator (dielectric), is disposed and patterned also by standard processing. The semiconductor channel material 5 is then deposited and this material's source and drain regions are formed by doping in the case of a standard inversion FET or Ohmic contacts are formed in the case of an AMOSFET (16). Interconnects are patterned as seen in FIG. 12 with the source 17 and 18 lines obviously isolated electrically from one another.

Pre-formed circuitry may also be used and positioned by stamping, as discussed for Example 1. In general, the required circuitry is formed before disposing the substrate 15 and before separation from the working substrate 10. All the probe finishing steps such as etching or etching and anodization (e.g., those of FIG. 11), if utilized to from the unique tip probe (FIG. 9) of this invention, are undertaken after separation from the working substrate 10.

The information gathered by the circuitry can be wirelessly transmitted with additional circuitry and/or can be used to construct an image. Such additional circuitry including antennas can be incorporated into the back of the device or located at the device filed periphery.

In general, the probe FETs of this example can be used to sense by using gate current or by using the charge sensitivity of the gate electrode structure to modulate the source-drain current. The latter offers the advantage of signal amplification. These FET probes may have the probe functionalized to enhance specificity and sensitivity.

Example 3

The probe structure of this invention can be used for nano- and micro-fluidic applications. In such an application, a material chosen for its bio-compatibility and processability is disposed into the nano- or micro-cavity 12 and surrounding regions in FIGS. 4B and 5A. The material and processing parameters are chosen so that the material does not fill in the cavity completely, but leaves a void in the center of the cavity as in the example of FIG. 10. The cross-sectional FESEM image in this figure shows the process step after the material 19-21 is disposed into, in this case, a nano-cavity. Next, the probe structures are separated from the substrate 10, and the tip of the probe 21 is selectively removed by etching down the mold and probe material to the level selected for the desired tip opening size. All the mold material is then subsequently removed. When the tip of the probe is removed, the probe structure forms a nano- (or micro) needle architecture. By building a nano- and/or microfluidic system onto or into the full base layer 16C prior to separation from substrate 10, the nano-/micro-needle creation outlined above can lead to the integration of nanoand/or micro-needle structures (or arrays of such structures) into nano- and/or micro-fluidic systems for analysis and/or removal or injection into body fluids or intercellular media. The overall architecture disclosed herein allows the integration of the bio-medical sensors of this invention with the fluidic systems of this example providing a path to intelligent drug delivery systems with built-in sensors and circuitry.

REFERENCES CITED

1. A. Grinvald, R. Hildesheim, VSDI: A New Era in Functional Imaging of Cortical Dynamics. *Nat. Rev. Neuroscience* 5, pp. 874-885 (2004)
2. M. Scanziani, M. Hausser, Electrophysiology in the Age of Light. *Nature* 461, pp. 930-939 (2009)
3. R. D. Purves, Microelectrode Methods for Intracellular Recording and Ionophoresis, *Academic Press*, London (1981)
4. B. Sakmann, E. Neher, Patch Clamp Techniques for Studying Ionic Channels m Excitable Membranes. *Annual Reviews Physio.* pp 455-472 (1984)
5. A. Molleman, *Patch Clamping: An Introductory Guide to Patch Clamp Electrophysiology*. Wiley, Chichester, UK (2003)
6. R. M. Wightman, Probing Cellular Chemistry m Biological Systems with Microelectrodes. *Science* 311, pp. 1570-1574 (2006)
7. A. G. Ewing, T. G. Strein, Y. Y. Lau, Analytical Chemistry in Microenvironments: Single Nerve Cells. *Ace. Chem. Research* 25, pp. 440-447 (1992)
8. M. G. Schrlau, N. J. Dun, H. H. Bau, Cell Electrophysiology with Carbon Nanopipettes. *ACS Nano* 3, pp. 563-568 (2009)
9. Bozhi Tian et al., Three-Dimensional, Flexible Nanoscale Field-Effect Transistors as Localized Bioprobes. *Science* 329, pp. 830-834 (2010)
10. Dae-Hyeong Kim and Jonathan Viventi et al., Dissolvable Films of Silk Fibroin for Ultrathin Conformal Biointegrated Electronics. *Nature Materials* 9, pp. 511-517 (2010)
11. J. F. Eschermann et al., Action Potentials of HL-1 Cells Recorded with Silicon Nanowire Transistors. *Applied Physics Letters* 95, Issue 8 pp. 083703-083703-3 (2009)
12. Q. Qing et al., Nanowire Transistor Arrays for Mapping Neural Circuits in Acute Brain Slices. *Proc. Natl. Acad. Sci. USA* 107, pp. 1882-1887 (2010)
13. I. Heller, W. T. T. Smaal, S. G. Lemay, C. Dekker. Probing Macrophage Activity with
14. W. Lu, C. M. Lieber, Nanoelectronics From the Bottom Up. *Nature Materials* 6, pp. 841-850 (2007)
15. Kim, S et al., Integrated Wireless Neural Interface Based on the Utah Electrode Array. *Biomed Microdevices* 11, pp. 453-466 (2009)
16. Stephen J. Fonash, MdMadh-hud Iqbal, Florin Udrea, and Piero Migliorato. Numerical Modeling Study of the Unipolar Accumulation Transistor. Applied Physics Letters, 91, No. 19, 193508 (2007); Md Mash-Hud Iqbal, Yi Hong, Pranav Garg, Florin Udrea, Piero Migliorato, and Stephen J. Fonash, "The Nanoscale Silicon Accumulation-Mode MOSFET-A Comprehensive Numerical Study", IEEE Transactions on Electron Devices, vol 55, No. 11, 2946-2959 (2008).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

The foregoing description is illustrative of particular embodiments of the invention, but is not meant to be a limitation upon the practice thereof. The following claims, including all equivalents thereof, are intended to define the scope of the invention.

The invention claimed is:

1. A three dimensional biomedical probe device comprising:
    a planar substrate;
    a probe structure supported on said planar substrate, said probe structure including a plurality of probes in an array, each probe of the plurality of probes being an electrical contact electrode or a transistor gate electrode, said probe structure further having a base from which each probe essentially perpendicularly extends for a length to a tip, a surface of the base at inter-probes regions being generally planar, each probe having a linear dimension at the tip in the range of 5 nanometers (nm) to 5 microns, the tips of the plurality of probes being a distal-most portion of the probe structure such that the probe structure is capable of contacting skin when the probe device is applied to the skin; and
    said probe structure having electrical connectivity for detecting and collecting current or voltage produced in a bio-medical medium between said probe structure and a reference electrode.

2. The device of claim 1, wherein probe shape, probe spacing and probe lattice positioning of said plurality of probes are constant with position or vary across the array.

3. The device of claim 2 further comprising connectivity for each of said plurality of probes of the array wherein each individual probe of said plurality of probes is independently electrically addressable;
    said connectivity controlled by a transistor at or part of each individual probe at a probe site, said transistor comprising a transistor gate electrode, a drain, a channel, a source, and a gate dielectric; and
    wherein all or less than all of the components of said transistor gate electrode, drain, channel, source, or gate dielectric are in underlying physical and electrical communication with said probe structure.

4. The device of claim 3 wherein said transistor establishes a data line for each of said probe sites.

5. The device of claim 3 farther comprising a driver line for each of said probe sites.

6. The device of claim 1 further comprising a plurality of molecules, a plurality of nanoparticles or a combination thereof functionalizing a surface of said probe structure.

7. The device of claim 1 wherein the composition of said probe structure comprises a metal, a semiconductor, or both.

8. The device of claim 1 further comprising an insulator sheath extending from the probe base along a portion of the length of said probe structure resulting in the probe tip region being solely in electrical communication with a bio-medical medium.

9. The device of claim 1 wherein said probe is a nano- or micro-electrode.

10. The device of claim 1 wherein said probe is the gate electrode of an FET device.

11. The device of claim 1 further comprising a microfluidic channel in fluid communication with said tip.

12. The device of claim 1, wherein the transistor gale electrode overlies and is in physical contact with a dielectric of a plurality of field effect transistors thereby enabling PET signal detection.

13. The device of claim 1, wherein the current is alternating current (AC) or direct current (DC).

14. The device of claim 1, wherein said probe structure having electrical connectivity for detecting and collecting transient signals produced in a bio-medical medium between said probe structure and a reference electrode.

15. The device of claim 1, wherein the plat substrate is flexible.

16. The device of claim 1, wherein each probe is column-shaped, cone-shaped, hemisphere-shaped or dome-shaped.

17. The device of claim 1, wherein each probe is hollow.

18. The device of claim 12 wherein said plurality field effect transistors are configured to form an addressable array of sensing probes.

19. The device of claim 18 further comprising circuitry for selectively addressing each of said plurality field effect transistors.

20. The device of claim 19 wherein said circuitry further comprises a signal amplification of an output from each probe device site.

21. The device of claim 12 further comprising a reference electrode, said reference electrode is located on said probe structure and is in electrical communication with a biological medium.

22. A process of sampling physiological activity of a biological medium comprising:
    providing a three dimensional biomedical probe device of claim 1;
    inserting said probe structure of the device of claim 1 into said medium for electrical contacting of said medium; and
    energizing the device to provide an electrical signal of the activity of the biological medium.

23. The process of claim 22 wherein said inserting into the biological medium further comprises a cell or cells and said insertion is done without lysis.

24. The process of claim 23 wherein the cell is a neuron.

25. The process of claim 22 wherein the electrical signal is a measure of medium potential, content, or electrical current signals.

* * * * *